US011006874B2

(12) United States Patent
Jayaraman et al.

(10) Patent No.: US 11,006,874 B2
(45) Date of Patent: May 18, 2021

(54) REAL-TIME STRESS DETERMINATION OF AN INDIVIDUAL (71) Applicant: Tata Consultancy Services Limited, Mumbai (IN)

(72) Inventors: Srinivasan Jayaraman, Bangalore (IN); Kriti Kumar, Bangalore (IN); Balamuralidhar Purushothaman, Bangalore (IN)

(73) Assignee: Tata Consultancy Services Limited, Mumbai Maharashtra (IN)

( * ) Notice: Subject to any disclaimer, the term of this patent is extended or adjusted under 35 U.S.C. 154(b) by 1516 days.

(21) Appl. No.: 13/965,523

(22) Filed: Aug. 13, 2013

(65) Prior Publication Data
US 2014/0046144 A1 Feb. 13, 2014

(30) Foreign Application Priority Data
Aug. 13, 2012 (IN) .............. 2357MUM2012

(51) Int. Cl.
*A61B 5/16* (2006.01)
*A61B 5/0245* (2006.01)
(Continued)

(52) U.S. Cl.
CPC .......... *A61B 5/165* (2013.01); *A61B 5/0006* (2013.01); *A61B 5/0077* (2013.01);
(Continued)

(58) Field of Classification Search
CPC ..... A61B 5/165; A61B 5/0006; A61B 5/0245; A61B 5/7253; A61B 5/7264;
(Continued)

(56) References Cited

U.S. PATENT DOCUMENTS 8,430,817 B1 * 4/2013 Al-Ali ................. A61B 5/7221
128/920
8,512,240 B1 * 8/2013 Zuckerman-Stark .... A61B 5/02
128/924
(Continued)

FOREIGN PATENT DOCUMENTS

WO   WO-2006/009830 A2    1/2006
WO   WO 2006009830 A2 *  1/2006 .......... A61B 5/0205
(Continued)

Primary Examiner — Gary Jackson
Assistant Examiner — Sebastian X Lukjan
(74) Attorney, Agent, or Firm — Schwegman Lundberg & Woessner, P. A.

(57) ABSTRACT

The present subject matter relates to a computer implemented method for real time determination of stress levels of an individual. The method includes receiving at least one stream of physiological data from at least one primary sensor for a predetermined duration, and preprocessing the at least one stream of physiological data to extract physiological parameters, where the preprocessing includes performing a preliminary analysis on the at least one stream of physiological data. The method further includes determining a stress level of the individual based on at least the physiological parameters, wherein the determining comprises performing a statistical analysis on the physiological parameters.

15 Claims, 4 Drawing Sheets (51) Int. Cl.
  *A61B 5/00* (2006.01)
  *A61B 5/11* (2006.01)
  *A61B 5/024* (2006.01)
  *G06K 9/00* (2006.01)
  *A61B 5/0205* (2006.01)
  *A61B 5/0456* (2006.01)
  *A61B 5/352* (2021.01)

(52) U.S. Cl.
  CPC .......... *A61B 5/0205* (2013.01); *A61B 5/0245* (2013.01); *A61B 5/02405* (2013.01); *A61B 5/1116* (2013.01); *A61B 5/352* (2021.01); *A61B 5/7253* (2013.01); *A61B 5/7264* (2013.01); *G06K 9/0053* (2013.01); *A61B 5/486* (2013.01); *A61B 2503/24* (2013.01); *A61B 2576/00* (2013.01); *G06K 2009/00939* (2013.01)

(58) Field of Classification Search
  CPC . A61B 5/1116; A61B 5/0456; A61B 5/02405; A61B 2576/00; A61B 2503/24; A61B 5/486; G06K 9/0053; G06K 2009/00939

USPC ........................................................ 600/301
  See application file for complete search history.

(56) References Cited

U.S. PATENT DOCUMENTS

2003/0214409 A1* 11/2003 Hickle .................. A61B 5/412
                                                340/573.1
  2007/0299876 A1* 12/2007 Welti ........................ A61B 5/16
  2009/0030289 A1* 1/2009 Katayama ............ A61B 5/0008
                                                600/301
  2012/0191147 A1* 7/2012 Rao ...................... A61B 5/1171
                                                607/3
  2012/0289794 A1* 11/2012 Jain ...................... A61B 5/0022
                                                600/301

FOREIGN PATENT DOCUMENTS

WO    WO-2008/057884 A2    5/2008
  WO    WO-2011/074004 A2    6/2011
  WO    WO-2012104658 A2 *  8/2012    .......... A61B 5/0006
  WO    WO-2013016007 A2 *  1/2013    .......... A61B 5/6889

* cited by examiner

REAL-TIME STRESS DETERMINATION OF AN INDIVIDUAL

CLAIM OF PRIORITY

This application claims the benefit of priority of Indian Patent Application Serial Number 2357/MUM/2012, entitled "REAL-TIME STRESS DETERMINATION OF AN INDIVIDUAL," filed on Aug. 13, 2012, the benefit of priority of which is claimed hereby, and which is incorporated by reference herein in its entirety.

TECHNICAL FIELD

The present subject matter, in general, relates to physiological data monitoring and, in particular, relates to determining stress levels in real time.

BACKGROUND

Physiological monitoring of an individual can be important in understanding an overall state of health of the individual. For example, it may be necessary to monitor physiological signals, such as electrocardiogram (ECG) signals, of an individual to ascertain a stress level of the individual. Solutions to monitor and measure the physiological signals include portable measurement devices, which can be coupled to a users outfit or body, to measure the physiological signals.

Current methods of physiological monitoring also include measuring the physiological signals over a duration of time, either by inducing stress among participants by making them undergo a stress test or perform a relaxation exercise, or directly from the body of the individual, for example, by electrodes, or sensors directly in contact with the skin of the individual, for obtaining an ECG plot. The plot is then further analyzed by a medical professional to decipher the state of health of the individual.

SUMMARY

This summary is provided to introduce concepts related to real-time stress determination, and the concepts are further described below in the detailed description. This summary is not intended to identify essential features of the claimed subject matter nor is it intended for use in determining or limiting the scope of the claimed subject matter.

The present subject matter relates to a computer implemented method for real time determination of stress levels of an individual. In one implementation, the method includes receiving at least one stream of physiological data from at least one primary sensor for a predetermined duration, and preprocessing the at least one stream of physiological data to extract physiological parameters, where the preprocessing includes performing a preliminary analysis on the at least one stream of physiological data. The method further includes determining a stress level of the individual based on at least the physiological parameters, wherein the determining comprises performing a statistical analysis on the physiological parameters.

In one implementation the present subject matter relates to a stress determination system for determining the stress of an individual in real time. In one implementation, the stress determination system includes a processor, and a memory coupled to the processor. The memory includes an ECG sensing module configured to receive at least one stream of physiological data from at least one primary sensor for a duration of approximately one minute, an analysis module configured to preprocess the at least one stream of physiological data to extract physiological parameters, and determine a stress level of the individual based on at least the physiological parameters.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Systems and methods for stress determination in real time are described therein. The systems and methods can be implemented in a variety of computing devices, such as laptops, desktops, workstations, tablet-PCs, smart phones, notebooks or portable computers, tablet computers, mainframe computers, mobile computing devices, entertainment devices, computing platforms, internet appliances and similar systems. However, a person skilled in the art will comprehend that the embodiment of the present subject matter are not limited to any particular computing system, architecture or application device, as it may be adapted to take advantage of new computing system and platform as they become accessible.

Physiological monitoring includes monitoring various physiological functions of the human body to determine an overall status of health of an individual. For example, a pulse of the individual may be measured over a period of time to determine how an individual is feeling, i.e. agitated, happy, stressed, etc. In another example, an Electrocardiogram (ECG) may be used to determine a human heart condition. In this example, sensors of the ECG can be attached to the human body and an output thereof, such as an ECG waveform, can be analyzed to understand the overall health of the individual.

Other conventional solutions for physiological monitoring include ambulatory measurement devices, which can measure vital signs of the individual for further calculations and analysis. These devices can be tedious to use as they have to be attached to the human body, by means of wires, tethering harnesses, duct tape, adhesive etc. and subsequently detached from the human body. Furthermore, in some instances, a minor level of stress or anxiety can be induced in the individual even due to the fact that he is aware of being tethered to such a device.

Other conventional physiological monitoring solutions include measurement devices integrated into various types of apparel, or accessories that can be worn on the human body, where sensors or sensing modules can be integrated therein. These sensors record and store data, which can later be analyzed by a medical practitioner, or the like. These conventional solutions are time intensive methods where substantially long durations of time are required to measure the data, and subsequently analyze the various outputs of the sensors, to finally determine the overall status of the individual's health.

The present subject matter describes systems and methods for measuring stress levels in real time. In one implementation, the system can include primary sensors such as Electrocardiogram (ECG) sensors to capture physiological data, such as cardiac signals, from sensors disposed in the surroundings, such as a local environment of an individual. Examples of the local environment can include a work environment, such as an office or a manufacturing unit, inside the cabin of a car, on various client devices, in a room of the individual, etc. For example, the primary sensors can be positioned or deployed in a working environment of the individual to capture the physiological data from the individual. For this purpose, depending on the type of sensor, the primary sensors can be in direct or indirect contact with the individual. For example, a dry electrode type sensor can be positioned such that it measures the cardiac signals when in contact with the individual's skin, such as a laptop touchpad, chair handle and so on. In another example, a capacitive type sensor can be integrated within the client device, such as a laptop touchpad, chair, or a smartphone touchscreen. For example, the individual can be in the vicinity of a chair, which has an electrode integrated in a backrest support on the lumbar region of the chair. In this case, the electrode can be configured to capture the cardiac signals.

In one implementation, the primary sensors can be provided in the form of a sensing unit that can be installed in the working environment of the individual, for example, desk, chair seat, steering wheel of vehicle, etc. In this manner, the individual need not be consciously aware of the presence of the sensors and can continue working according to his daily routine. Furthermore, in this way, an unbiased and accurate capture of the physiological data of the individual can be facilitated.

In one implementation, the system according to the present subject matter is configured to capture the cardiac signals in real time via the primary sensors for a predefined duration, for example of approximately one minute or more. This means that the cardiac signals of the individual can be captured by the primary sensors for approximately one minute before further calculations and analysis are carried out to determine a final stress level of the individual. In a further implementation, the primary sensors can be configured to capture more than one sample of physiological data for greater accuracy of stress determination.

In another implementation, supplementary to the cardiac signals captured by the ECG sensors, supplementary physiological data can be captured to aid in the determination of the final stress level. For example, secondary sensors from client devices, such as smart phones, laptops, and personal computers can be used to capture the supplementary physiological data. Examples of the supplementary physiological data include data from accelerometer sensors, barometer sensors, and webcam or camera sensors. Further information can be derived from the supplementary physiological data to aid and enhance the accuracy of the stress determination of the individual.

In one implementation, the supplementary physiological data is captured in addition to the cardiac signals based on a threshold time limit. For example, the threshold time limit can be one minute, and in case the cardiac signals from the primary signals are received for less than one minute, the supplementary physiological data can be captured and utilized for the stress determination process.

In one implementation, the physiological data captured by the primary sensors can be preprocessed. The preprocessing includes filtering to reduce noise, and in cases of where more than one data sample is captured from the primary sensors, the preprocessing can include comparative analysis with the subsequent readings to determine a deviation in the readings if any. In this manner, a possibility of error can be reduced, as well as the efficiency by which the final determination of stress is carried out can be increased. In one implementation, the preprocessing includes performing a preliminary analysis on the received physiological data. This preliminary analysis includes waveform analysis to detect R-peaks from the ECG sensor input, i.e. an ECG waveform, calculating duration between subsequent R-peaks, frequency domain analysis, and time domain analysis to extract physiological parameters from the physiological data. The physiological parameters are indicative of a heart condition of the individual.

In one example, the preprocessing can be performed by a stress determination system, which for example, can be located in a plurality of locations, such as a remote server, or even the client device itself. In another example, the stress determination system can include the primary sensors, where the stress determination system can be configured to determine the stress level of the individual.

In one example, the stress determination system can be configured to query a database to verify if the individual is a first time user. If so, then the extracted physiological parameters can be stored in the database for easy accessibility and reference. For example, the individual may be passively assigned a reference ID, with which he will be identified and his profile updated, for every subsequent stress determination process.

In one implementation, the stress determination system utilizes the physiological parameters to determine the stress level of the individual. For example, the stress determination system can be configured to perform a statistical analysis on the physiological parameters based on a classifying technique, or matching technique to determine the stress level. In a further implementation, the stress determination system can be configured to utilize the supplementary physiological data along with the preprocessed data to determine the stress level. For example, the supplementary physiological data can be utilized only on fulfillment of a certain condition, such as in a case where the duration of time for capturing the physiological data is less than one minute. Therefore, in order to reinforce the stress determination process, or in order to enhance the accuracy of determination of the stress level, the stress determination system can be configured to also use the supplementary physiological data.

In one implementation, the stress determination system can be configured to forward the stress levels to a remote server for further study, or clinical analysis. In a further implementation, the stress determination system can transmit the stress levels to a display module for information of the individual. For example, in case the stress determination system is part of the client device, the stress determination system can transmit the stress levels to a display screen of the client device.

The stress determination system can be implemented in a plurality of configurations, which facilitates portability, realtime and time efficient determination of stress levels. Furthermore, as described above, the determination of stress can be facilitated in an accurate and passive manner, where physiological data as well as supplementary physiological data can be captured from the working environment of the individual without active intervention of, or participation by the individual.

These and other advantages of the present subject matter would be described in greater detail in conjunction with the following figures. While aspects of described systems and methods for stratified sampling of a database can be implemented in any number of different computing systems, environments, and/or configurations, the embodiments are described in the context of the following exemplary system(s).

Figure 1:
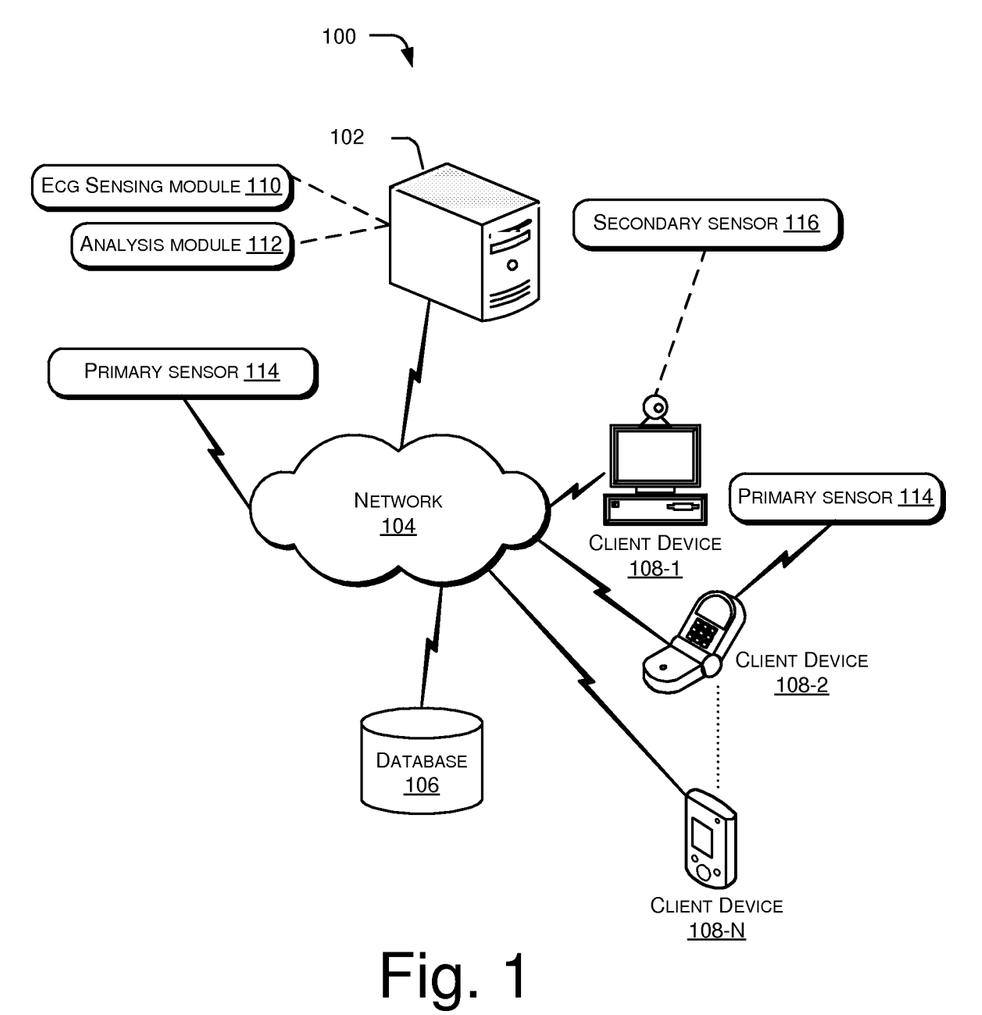
FIG. 1 illustrates a network environment implementing a stress determination system, in accordance with an embodiment of the present subject matter.

FIG. 1 illustrates a network environment 100 implementing a stress determination system 102, according to an embodiment of the present subject matter. In the network environment 100, the stress determination system 102 is connected to a network 104. Furthermore, a database 106, and one or more client devices 108-1, 108-2 . . . 108-N, collectively referred to as client devices 108, are also connected to the network 104.

The stress determination system 102 can be implemented as any computing device connected to the network 104. In one example, the stress determination system 102 can be embodied integrally with the database 106. In one instance, the stress determination system 102 may be implemented as mainframe computers, workstations, personal computers, desktop computers, multiprocessor systems, laptops, network computers, minicomputers, servers and the like. In addition, the stress determination system 102 may include multiple servers to perform mirrored tasks for users, thereby relieving congestion or minimizing traffic.

Furthermore, the stress determination system 102 can be connected to the client devices 108 through the network 104. Examples of the client devices 108 include, but are not limited to personal computers, desktop computers, smart phones, PDAs, and laptops. Communication links between the client devices 108 and the stress determination system 102 are enabled through a desired form of connections, for example, via dial-up modem connections, cable links, digital subscriber lines (DSL), wireless or satellite links, or any other suitable form of communication. In one implementation, the stress determination system 102 can be provided internal to the client devices 108. In this manner, the functionality of the stress determination system 102 can be provided along with the functionality of the client devices 108.

Moreover, the network 104 may be a wireless network, a wired network, or a combination thereof. The network 104 can also be an individual network or a collection of many such individual networks interconnected with each other and functioning as a single large network, e.g., the internet or an intranet. The network 104 can be implemented as one of the different types of networks, such as intranet, local area network (LAN), wide area network (WAN), the internet and such. The network 104 may either be a dedicated network or a shared network, which represents an association of the different types of networks that use a variety of protocols, for example, Bluetooth, Hypertext Transfer Protocol (HTTP), Transmission Control Protocol/Internet Protocol (TCP/IP), etc., to communicate with each other. Further, the network 104 may include network devices, such as network switches, hubs, routers, host bus adapters (HBAs), for providing a link between the stress determination system 102 and the client devices 108. The network devices within the network 104 may interact with the stress determination system 102 and the client devices 108 through communication links.

In one implementation, the stress determination system 102 includes an ECG sensing module 110 and an analysis module 112. In one implementation, the ECG sensing module 110 can be configured to receive signals from one or more primary sensors 114 that can be disposed in a work environment of an individual. For example, the primary sensors 114 can be disposed on a steering wheel of a car, a chair which the individual uses, a work desk, laptop, personal computer etc. In one implementation, the primary sensors 114 can then transmit physiological data, which includes ECG waveforms to the ECG sensing module 110 for further analysis thereof. In one example, the primary sensors 114 can be configured to capture the physiological data for duration of 1 minute or more. In this manner, the system functions in a time efficient manner and passive manner to determine the stress levels of the individual, thereby not requiring an active intervention or participation of the individual.

In one implementation, the analysis module 112 can be configured to obtain the physiological data received by the ECG sensing module 110 and preprocess the physiological data. The preprocessing is performed to enhance the quality of the physiological data for further analysis. Furthermore, the analysis module 112 can be configured to determine a stress level of the individual based on the preprocessed data. Moreover, based on certain conditions, the analysis module 112 can be configured to utilize supplementary physiological data to further increase the accuracy of the stress determination process. For example, as shown in FIG. 1, the client devices 108 can be implemented with secondary sensors 116, which capture the supplementary physiological data from the working environment of the individual, and transmit the supplementary physiological data via the network 104, to the stress determination system 102. The supplementary physiological data can include but is not limited to accelerometer sensor data, barometer sensor data, webcam sensor data, and camera sensor data.

Furthermore, based on the preprocessed data and the supplementary physiological data, the stress determination system 102 can be configured to determine the stress level of the individual. For example, the analysis module 112 can be configured to perform a statistical analysis on the preprocessed data and the supplementary physiological data to determine the stress level. Further details regarding the stress determination are provided in the detailed description associated with FIG. 2.

Figure 2:
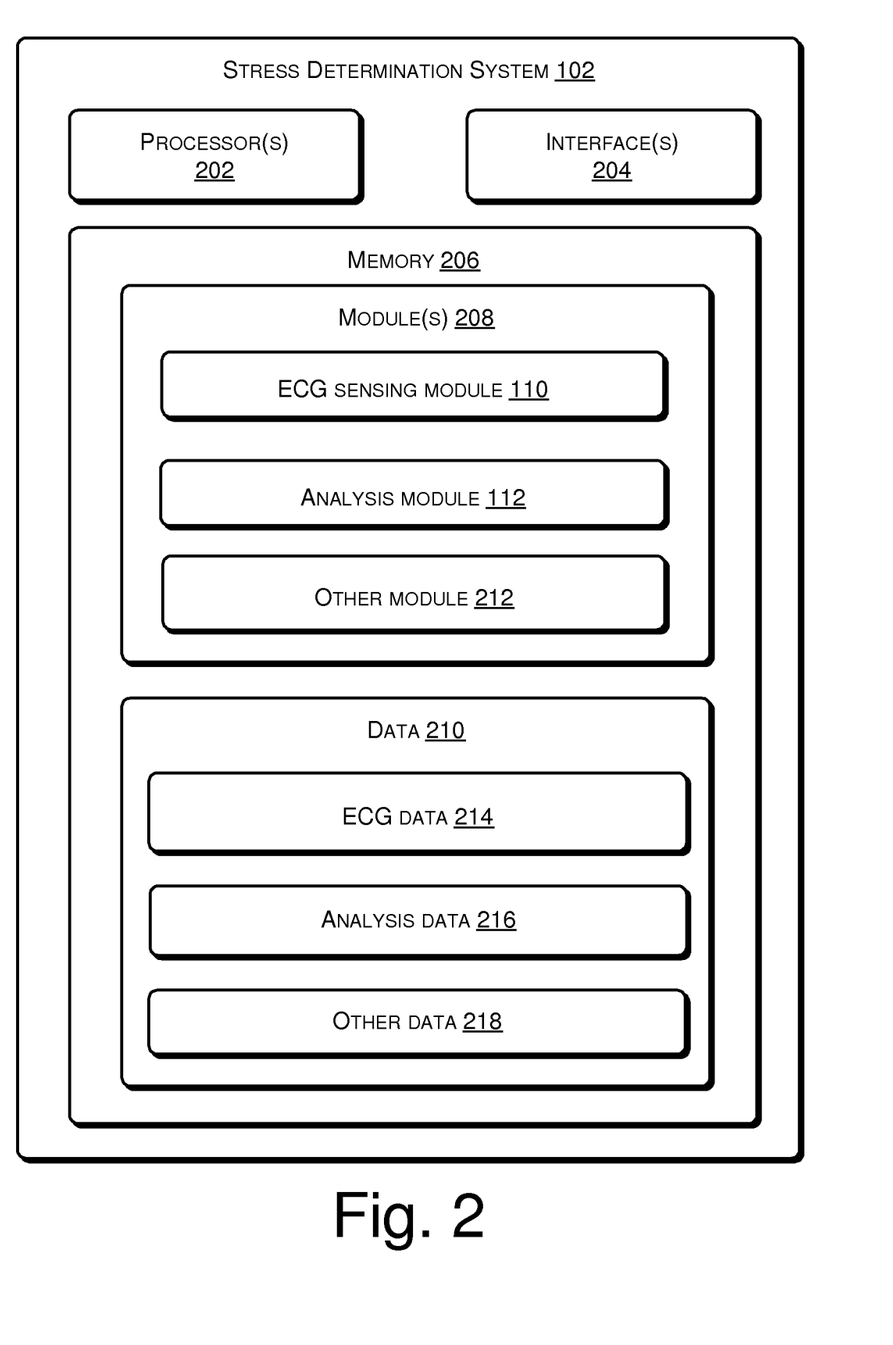
FIG. 2 illustrates a stress determination system for measuring stress values in real time, in accordance with an embodiment of the present subject matter.

FIG. 2 illustrates the stress determination system 102, in accordance with an embodiment of the present subject matter. In said implementation, the stress determination system 102 includes one or more processor(s) 202, interface(s) 204, and a memory 206 coupled to the processor 202. The processor 202 can be a single processing unit or a number of units, all of which could also include multiple computing units. The processor 202 may be implemented as one or more microprocessors, microcomputers, microcontrollers, digital signal processors, central processing units, state machines, logic circuitries, and/or any devices that manipulate signals based on operational instructions. Among other capabilities, the processor 202 is configured to fetch and execute computer-readable instructions and data stored in the memory 206.

The interfaces 204 may include a variety of software and hardware interfaces, for example, interface for peripheral device(s), such as a keyboard, a mouse, an external memory, and a printer. Further, the interfaces 204 may enable the stress determination system 102 to communicate with other computing devices, such as web servers and external data repositories in the communication network (not shown in the figure). The interfaces 204 may facilitate multiple communications within a wide variety of protocols and networks, such as a network, including wired networks, e.g., LAN, cable, etc., and wireless networks, e.g., WLAN, cellular, satellite, etc. The interfaces 204 may include one or more ports for connecting the stress determination system 102 to a number of computing devices.

The memory 206 may include any computer-readable medium known in the art including, for example, volatile memory, such as static random access memory (SRAM) and dynamic random access memory (DRAM), and/or nonvolatile memory, such as read only memory (ROM), erasable programmable ROM, flash memories, hard disks, optical disks, and magnetic tapes. The memory 206 also includes module(s) 208 and data 210.

The module(s) 208 include routines, programs, objects, components, data structures, etc., which perform particular tasks or implement particular abstract data types. In one implementation, the module(s) 208 includes the ECG sensing module 110, the analysis module 112, and other module(s) 212. The other module(s) 212 may include programs or coded instructions that supplement applications and functions of the stress determination system 102.

On the other hand, the data 210, inter alia serves as a repository for storing data processed, received, and generated by one or more of the module(s) 208. The data 210 includes for example, ECG data 214, analysis data 216, and other data 218. The other data 218 includes data generated as a result of the execution of one or more modules in the module(s) 208.

In one implementation, the stress determination system 102 can be configured to determine the stress level of an individual from his work environment. For example, by utilizing physiological data captured by the primary sensors 114, and supplementary physiological data captured by secondary sensors 116, the stress determination system 102 can be configured to determine the stress level of the individual in real-time and forward information pertaining to the stress level for further clinical analysis and study. In this manner, the real-time stress determination facilitates a better understanding of day to day stress experienced by the individual, in everyday work conditions.

In one implementation, the primary sensors 114 can be ECG sensors that are configured to capture and transmit at least one stream of the physiological data, such as cardiac signals of the individual. The primary sensors 114 can be embodied as dry electrode type sensors, which can be positioned such that they capture the cardiac signals when in contact with the individual's skin. In another example, the primary sensors 114 can be embodied as capacitive type sensors, which can be integrated within one of the client devices 108, such as a laptop touchpad, or a smartphone touchscreen, where the primary sensors 114 capture the cardiac signals when the user is using said client devices 108. Therefore, when the individual is involved in the course of his routine work, the primary sensors 114 can be configured to capture the cardiac signals of the individual and transmit them to the ECG sensing module 110 of the stress determination system 102. In one example, the primary sensors 114 can be configured to capture a first stream of the physiological data for a predetermined duration, for example of one minute or more, and shortly afterwards, capture a second stream of the physiological data of the same duration. The first and the second streams of physiological data can be referred to collectively as simply the physiological data. The ECG sensing module 110 can be configured to receive the first and second streams of physiological data from the primary sensors 114 and store the physiological data in the ECG data 214.

In one example, the ECG sensing module 110 can be configured to query an external database, such as the database 106, to verify whether the physiological data corresponds to an already existing individual. For example, for a first time user, the ECG sensing module 110 can be configured to generate an ID number, and link said ID number to an individual profile in the database 106. Upon receiving further physiological data against an already existing ID number, the ECG sensing module 110 can be configured to update the individual profile linked with that ID number.

In one implementation, the analysis module 112 can be configured to fetch the first and the second streams of physiological data from the ECG data 214 or in certain cases from the database 106, for preprocessing. In one example, the analysis module 112 can be configured to filter the physiological data to reduce noise and enhance the quality of the physiological data for further processing. The physiological data can include ECG signals, and the analysis module 112 can be configured to detect R peaks in the ECG signals and the durations between subsequent R-peaks. Where there is more than one stream of physiological data, the analysis module 112 can be configured to compare the two waveforms thereof to determine a deviation if any. Furthermore, time durations between subsequent R-peaks can also be determined in the preprocessing stage. The analysis module 112 can be configured to preprocess the physiological data to extract one or more physiological parameters, which can be utilized to determine the stress level.

In one implementation, during the preprocessing, the analysis module 112 can be configured to perform a preliminary analysis on the physiological data. The preliminary analysis can include a frequency domain analysis, or a time domain analysis to extract the physiological parameters. The frequency domain analysis can include transforming the waveform in a frequency domain and then performing a pattern recognition technique, and the time domain analysis can include transforming the waveform in a time domain, and performing root mean square calculations, and standard deviation computations. For example, the analysis module 112 can be configured to extract a Root Mean Square of Successive Differences (RMSSD) from the physiological data by performing a time domain transformation. In this manner, the physiological data can be preprocessed to extract the physiological parameters. Furthermore, the analysis module 112 can be configured to store the physiological parameters in the analysis data 216.

In one implementation, the analysis module 112 can be configured to determine the stress level of the individual based on the extracted physiological parameters, as well as supplementary physiological data. In one implementation, the supplementary physiological data is utilized for the stress determination based on a threshold time limit to aid and enhance the accuracy of the stress determination. In one example, the supplementary physiological data can be received from the secondary sensors 116 as disclosed earlier. The supplementary physiological data can include information pertaining to a body posture and facial expression of the individual during the time of capture of the physiological data by the primary sensors 114. The secondary sensors 116, as described earlier, can be embodied in any of the client devices 108. For example, a webcam affixed to a laptop can be utilized to scan the facial expression of the individual, and transmit information pertaining to the facial expression to the analysis module 112. The analysis module 112 can then compare the facial expression with reference expressions, and how the facial expression varies over time, to determine approximately how the individual was feeling, i.e., happy, frustrated, confused, indifferent, etc. Accordingly, weighing factors can be associated with the facial expressions, which correspondingly affect the overall stress level determination. In a similar manner, accelerometer sensor data from a secondary sensor 116, say in a smartphone can be utilized to gain relevant information pertaining to a body posture or movement of the individual. This can then further be transmitted as supplementary physiological data to the analysis module 112 for the stress determination.

In one example, the supplementary physiological data can be considered for the stress determination, contingent on the threshold time limit. The threshold time limit, for example, can be configured as one minute, where in case less than one minute of physiological data is received from the primary sensors 114, the analysis module 112 can be configured to utilize the supplementary physiological data as well. In this manner, the stress determination process can be reinforced with additional data to determine a substantially accurate stress level of the individual.

In one implementation, based on the physiological parameters, and conditionally the supplementary physiological data, the analysis module 112 can be configured to determine the stress level of the individual. For example, depending on the physiological parameters extracted from the preprocessed data, such as Heart Rate Variability (HRV) information (root mean square of the squared difference of successive heart beats), the analysis module 112 can be configured to determine the stress level of the individual.

In one example, the analysis module 112 can be configured to fetch the physiological parameters from the analysis data 216 and perform a statistical analysis on the physiological parameters. The statistical analysis can be based on a classifier technique, and a matching technique. For example, the analysis module 112 can be configured to classify the various physiological parameters as a positive stress value, or a negative stress value. As in the example described earlier, for an RMSSD physiological parameter, the analysis module 112 can be configured to classify a negative slope as a positive stress value, and a negative slope as a negative stress value (meaning the individual is performing well).

In one example, the analysis module 112 can be configured to consider an initial reading or enrolled data as a baseline, or reference reading. Furthermore, the rest of the readings will be compared with the baseline reading to assess the deviation if any as a positive or negative stress value. For example, if the statistical value is $p<0.05$, then it is counted as a significant result. Therefore, the successive reading is considered to be significantly different from the baseline reading.

In another example, the analysis module 112 can be configured as a moving probe or window to compare successive readings to a baseline window of 1 minute of physiological data. Depending on the difference between the moving window and the baseline window, the analysis module 112 can classify the readings as a positive stress value, or a negative stress value. A confidence interval of 95% is taken for this statistical analysis, so whenever the statistical value is $p<0.05$ (corresponding to 95% confidence interval), a transition in the state of the stress levels of the individual is confirmed.

In yet another implementation, the analysis module 112 can be configured to derive positive or negative correlation coefficients based on a correlation between the moving window and the baseline window. Furthermore, based on the correlation coefficients, the analysis module 112 can be configured to detect a positive or a negative stress value of the individual.

In a further implementation, the analysis module 112 can be configured to compare the analyzed physiological parameters with existing records in a database, such as the database 106, based on the reference ID number. Furthermore, a profile of an individual can also be identified based on their own ECG signals. In one example, the reference records can be used as a baseline, with which subsequent parameters can be compared. The analysis module 112 can then classify the deviations as a positive or negative stress, depending on the quantum of deviation thereof from the reference records.

In case the threshold time limit condition is triggered, the supplementary physiological data can also be utilized. In one implementation, the analysis module 112 can be configured to store the stress level in the analysis data 216, or the database 106. Furthermore, based on the verification of the ID numbers as described earlier, the stress level can be updated in the relevant user profile.

In one implementation, the analysis module 112 can be configured to trigger an application for relaxing the individuals based on an individual's stress level. In one example, the application can be a third party software application provided on the client devices 108. If a stress level of the individual is above a threshold value or critical value, the analysis module 112 can be configured to trigger said application. The application can be configured to display audio-visual media based on individual preference. For example, the audio-visual media can be a humorous image or video clip. In such a manner, the stress determination system 102 can be configured to reduce the stress levels of the individual.

Figure 3A:
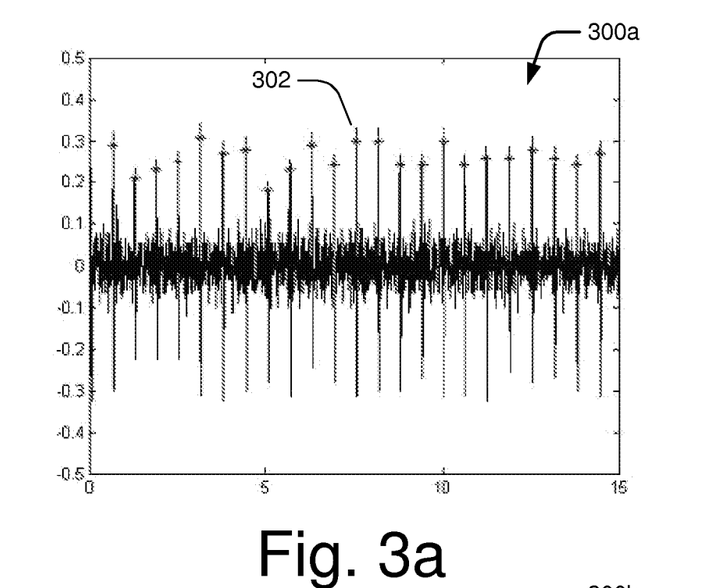
FIG. 3a illustrates an output of physiological data from a primary sensor in the form of a graph, in accordance with an embodiment of the present subject matter.
Figure 3B:
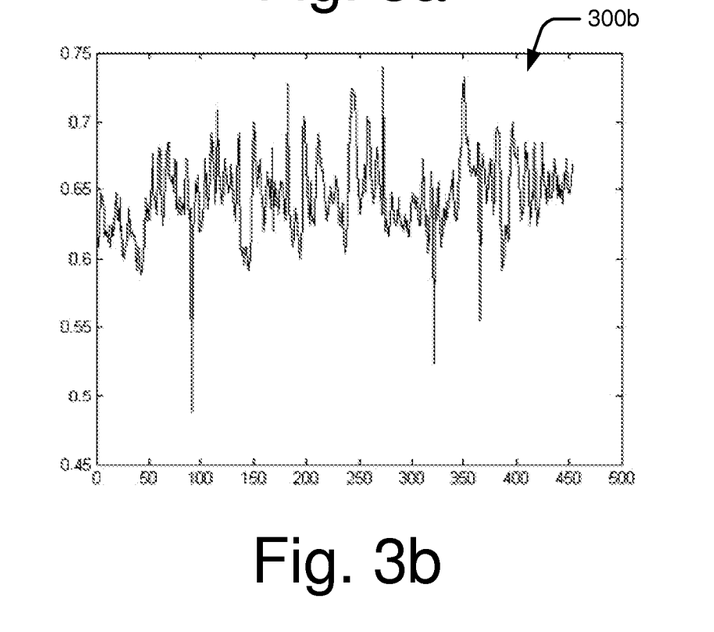
FIG. 3b illustrates a plot for computation of duration between R-peaks from the physiological data, in accordance with an embodiment of the present subject matter.

FIGS. 3a and 3b illustrate stages of a working example of stress determination, in accordance with an embodiment of the present subject matter.

FIG. 3a illustrates a stage of preprocessing, where an output of physiological data from the primary sensors 114 is preprocessed in accordance with an embodiment of the present subject matter. In said embodiment, the physiological data is in the form of an ECG waveform 300a. In the FIG. 3a, amplitude is plotted on the Y-axis, and time is plotted on the X-axis. In one example, the ECG waveform 300a of mV signal can be amplified to voltage signal X (n).

In one embodiment, as disclosed earlier, at the preprocessing stage, the stress determination system 102 can be configured to detect R-peaks 302 in the ECG waveform 300a.

FIG. 3b illustrates a further stage of preprocessing, where the duration between the R-peaks 302 is calculated. In one embodiment, the stress determination system 102 can be configured to calculate the duration between the subsequent R-peaks 302, as detected in FIG. 3a. In this figure, a graph 300b is illustrated, where a number of R-R intervals are plotted over the X-axis, and amplitude of the wave is plotted over the Y-axis.

Table 1 below illustrates physiological parameters that are extracted from the preprocessing stage. For example, from the graph shown in FIG. 3b, the stress determination system 102 can be configured to extract the following physiological parameters in order to determine the stress level of the individual.

TABLE 1

| Parameters | 1 min Interval |
|---|---|
| Mean RR | 721.39 ± 32.72 |
| Mean HR | 84.58 ± 3.91 |
| SDNN | 49.55 ± 5.92 |
| RMSSD | 55.62 ± 8.55 |
| NN50 Count | 77.33 ± 15.91 |
| pNN50 | 0.2 ± 0.04 |
| HRV Index | 17.05 ± 1.93 |
| VLF | 227.17 ± 35.43 |
| LF | 333.51 ± 71.83 |
| HF | 475.4 ± 121.45 |
| Total Power | 2729.16 ± 583.11 |
| LF/HF | 0.77 ± 0.11 |
| LFnu | 0.13 ± 0.02 |
| HFnu | 0.18 ± 0.01 |

In one implementation, the analysis module 112 can be configured to extract the physiological parameters based on a frequency domain analysis or a time domain analysis as described earlier. The analysis module 112 can further be configured to store the extracted physiological parameters in the analysis data 216, or an external database, such as the database 106.

Furthermore, once the physiological parameters are extracted, the analysis module 112 of the stress determination system 102 can be configured to determine the stress level, based on the statistical analysis. The statistical analysis includes a classifier technique, and a matching technique, as disclosed earlier.

Figure 4:
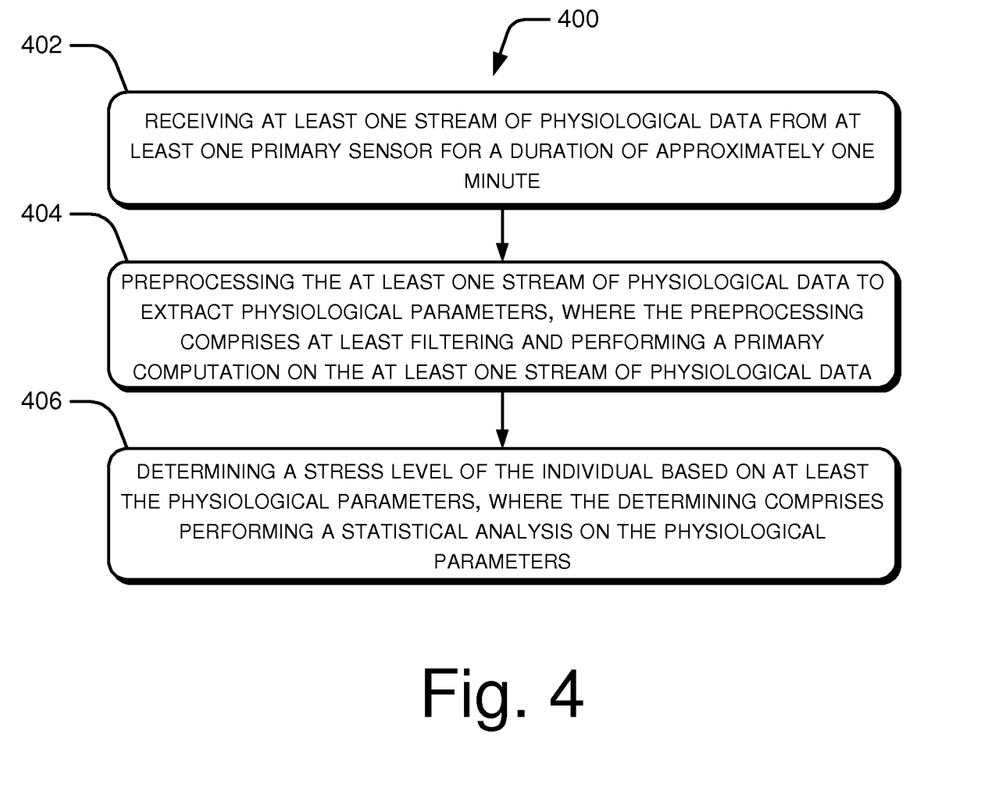
FIG. 4 illustrates a method for determining stress levels of an individual, in accordance with an embodiment of the present subject matter.

FIG. 4 illustrates a method 400 for determining stress levels of an individual, according to one embodiment of the present subject matter. The method 400 may be implemented in a variety of computing systems in several different ways. For example, the method 400, described herein, may be implemented using the stress determination system 102, as described above.

The method 400, completely or partially, may be described in the general context of computer executable instructions. Generally, computer executable instructions can include routines, programs, objects, components, data structures, procedures, modules, functions, etc., that perform particular functions or implement particular abstract data types. A person skilled in the art will readily recognize that steps of the method can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of the described method 400.

The order in which the method 400 is described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the methods can be implemented in any suitable hardware, software, firmware, or combination thereof. It will be understood that even though the method 400 is described with reference to the stress determination system 102, the description may be extended to other systems as well.

At block 402, one or more streams of physiological data, such as cardiac signals, can be received from one or more primary sensors. As disclosed earlier, the primary sensors can be of a dry or capacitive type, and can be deployed in a workplace environment, or a client device, such as the client devices 108. The workplace environment of an individual can be an office desk, chair, steering wheel of vehicle, etc. Therefore, depending on the type of sensor, the sensor can measure and transmit the physiological data for further processing. In one example, more than one sample of the physiological data can be measured and transmitted. Furthermore, as disclosed earlier, an ECG sensing module 110 of a stress determination system 102 can be configured to receive the one or more streams of physiological data from the one or more primary sensors.

At block 404, the physiological data can be preprocessed to extract physiological parameters. The physiological parameters are parameters that are indicative of a heart rate of an individual and can be utilized to determine the stress level of the individual in real-time. As described previously, the preprocessing includes a preliminary analysis of the physiological data. In one example, the preliminary analysis includes filtering the physiological data to increase the quality of the data for further processing, detecting R-peaks in the at least one stream of physiological data, and calculating duration between subsequent R-peaks to extract the physiological parameters. The preliminary analysis also includes performing a frequency domain analysis and a time domain analysis on the physiological data. In one implementation, an analysis module 112 of a stress determination system 102 can be configured to extract the physiological parameters from the physiological data.

At block 406, the stress level can be determined from the physiological parameters and contingently on supplementary physiological data. The determination of stress includes performing a statistical analysis on the physiological parameters, where the statistical analysis includes a classifier technique, or a matching technique. Moreover, if the physiological data is received for less than one minute in the block 402, the supplementary physiological data can be utilized to enhance the accuracy of the stress determination process. For example, information relating to the posture of the individual, and the facial expression of the individual can be part of the supplementary physiological data, and can be used in addition to the physiological data for the stress determination process. In one example, the analysis module 112 of the stress determination system 102 can be configured to determine the stress based on at least the physiological parameters using the classifier technique, or the matching technique. Once the stress levels are determined, the stress levels can be forwarded for further clinical analysis or study.

Although implementations of real-time stress determination of an individual have been described in language specific to structural features and/or methods, it is to be understood that the present subject matter is not necessarily limited to the specific features or methods described. Rather, the specific features and methods are disclosed as implementations for stratified sampling of a database.

We claim:

1. A computer implemented method for real time determination of stress level of an individual, the method comprising:

receiving, by an Electrocardiogram (ECG) sensing module, a first stream of physiological data from at least one primary sensor for a predefined duration and a second stream of physiological data after the first stream of physiological data from the at least one primary sensor for the predefined duration, wherein the at least one primary sensor is deployed in at least one of a workplace environment and a client device;

preprocessing, by an analysis module, the first stream of physiological data and the second stream of physiological data to extract physiological parameters by performing a preliminary analysis on the first stream of physiological data and the second stream of physiological data; and determining, by the analysis module, a stress level of the individual by performing a statistical analysis on the physiological parameters and supplementary physiological data, wherein the supplementary physiological data is received from at least one secondary sensor at same time of receiving the first stream of physiological data and the second stream of physiological data, wherein the supplementary physiological data is captured from the working environment of the individual without active intervention of the individual and is considered for determining the stress level of the individual only when a duration of receiving the first stream of physiological data and the second stream of physiological data from the at least one primary sensor is less than the predefined duration, wherein the analysis module classifies the physiological parameters as a positive stress value or a negative stress value by a moving probe or window to compare successive readings to a baseline window of the predefined duration of the physiological data, and depending on a difference between the moving window and the baselines window, the analysis module classifies the readings as the positive stress value or the negative stress value, wherein a confidence level is considered for the statistical analysis and a transition in a state of the stress level of the individual is confirmed when a statistical value is less than a threshold, wherein the individual is assigned an identification number and linked to a profile in a database, and further the profile is updated with determined stress level of the individual.

2. The method as claimed in claim 1, wherein the first stream of physiological data and the second stream of physiological data comprises an ECG signal.

3. The method as claimed in claim 1, wherein the preliminary analysis comprises:
filtering the first stream of physiological data and the second stream of physiological data to reduce noise;
detecting R-peaks in the first stream of physiological data and the second stream of physiological data;
calculating duration between subsequent R-peaks; and
extracting the physiological parameters from the duration between the R-peaks.

4. The method as claimed in claim 3, wherein the extracting further comprises performing one of a frequency domain analysis and a time domain analysis on the first stream of physiological data and the second stream of physiological data.

5. The method as claimed in claim 1, wherein the statistical analysis is based on at least one of a classifier technique, and a matching technique.

6. The method as claimed in claim 1, wherein the predefined duration is one minute.

7. The method as claimed in claim 1, wherein the supplementary physiological data includes data from accelerometer sensors, barometer sensors, and camera sensors of one or more client devices.

8. The method as claimed in claim 1, wherein the determining further comprises comparing the analyzed physiological parameters with existing records in a database, based on the individual reference identification number.

9. The method as claimed in claim 1, wherein the determining further comprises comparing the analyzed physiological parameters with existing records in a database, based on a recorded ECG signal.

10. A stress determination system for determining a stress level of an individual in real time, the stress determination system comprising:
a processor; and
a memory coupled to the processor, the memory comprising:
an Electrocardiogram (ECG) sensing module configured to receive a first stream of physiological data from at least one primary sensor for a duration of one minute and a second stream of physiological data after the first stream of physiological data from the at least one primary sensor for one minute, wherein the at least one primary sensor is deployed in at least one of a workplace environment and a client device;
an analysis module configured to:
preprocess the first stream of physiological data and the second stream of physiological data to extract physiological parameters; and
determine a stress level of the individual based on at least the physiological parameters and supplementary physiological data, wherein the supplementary physiological data is received from at least one secondary sensor at same time of receiving the first stream of physiological data and the second stream of physiological data, wherein the supplementary physiological data is captured from the working environment of the individual without active intervention of the individual and is considered for determining the stress level of the individual only when a duration of receiving the first stream of physiological data and the second stream of physiological data from the at least one primary sensor is less than one minute, wherein the analysis module classifies the physiological parameters as a positive stress value or a negative stress value by a moving probe or window to compare successive readings to a baseline window of one minute of the physiological data, and depending on a difference between the moving window and the baselines window, the analysis module classifies the readings as the positive stress value or the negative stress value, wherein a confidence level is considered for the statistical analysis and a transition in a state of the stress level of the individual is confirmed when a statistical value is less than a threshold,
wherein the individual is assigned an identification number and linked to a profile in a database, and further the profile is updated with determined stress level of the individual.

11. The stress determination system as claimed in claim 10, wherein the at least one primary sensor is one of a dry type sensor and a capacitive type sensor.

12. The stress determination system as claimed in claim 10, wherein the analysis module is further configured to compare the analyzed physiological parameters with existing records in a database, based on a reference identification number.

13. The stress determination system as claimed in claim 10, wherein the supplementary physiological data includes data from accelerometer sensors, barometer sensors, and camera sensors of one or more client devices.

14. The stress determination system as claimed in claim 10, wherein the analysis module is configured to trigger an application to relax the individual based on the determined stress level, and wherein the application comprises audio-visual media personalized by the individual.

15. A non-transitory computer-readable medium having embodied thereon a computer program for executing a method comprising:
   receiving a first stream of physiological data pertaining to an individual from at least one primary sensor for a duration of one minute and a second stream of physiological data after the first stream of physiological data from the at least one primary sensor for one minute, wherein the at least one primary sensor is deployed in at least one of a workplace environment and a client device;
   preprocessing the first stream of physiological data and the second stream of physiological data to extract physiological parameters by performing a preliminary analysis on the first stream of physiological data and the second stream of physiological data; and
   determining a stress level of the individual by performing a statistical analysis on the physiological parameters and supplementary physiological data, wherein the supplementary physiological data is received from at least one secondary sensor at same time of receiving the first stream of physiological data and the second stream of physiological data, wherein the supplementary physiological data is captured from the working environment of the individual without active intervention of the individual and is considered for determining the stress level of the individual only when a duration of receiving the first stream of physiological data and the second stream of physiological data from the at least one primary sensor is less than one minute, wherein the analysis module classifies the physiological parameters as a positive stress value or a negative stress value by a moving probe or window to compare successive readings to a baseline window of one minute of the physiological data, and depending on a difference between the moving window and the baselines window, the analysis module classifies the readings as the positive stress value or the negative stress value, wherein a confidence level is considered for the statistical analysis and a transition in a state of the stress level of the individual is confirmed when a statistical value is less than a threshold,
wherein the individual is assigned an identification number and linked to a profile in a database, and further the profile is updated with determined stress level of the individual.

* * * * *